US00PP31848P2

(12) United States Plant Patent
Lim

(10) Patent No.: US PP31,848 P2
(45) Date of Patent: Jun. 9, 2020

(54) ***ROSA HYBRIDA* PLANT NAMED 'ALTLAND'**

(50) Latin Name: *Rosa hybrida*
Varietal Denomination: ALTland

(71) Applicant: Altman Specialty Plants, Inc, Vista, CA (US)

(72) Inventor: Peter Lim, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 16/350,556

(22) Filed: Nov. 30, 2018

(51) Int. Cl.
*A01H 5/02* (2018.01)
*A01H 6/74* (2018.01)

(52) U.S. Cl.
USPC ..... Plt./148
CPC ..... *A01H 6/749* (2018.05)

(58) Field of Classification Search
USPC ..... Plt./148
CPC ..... A01H 6/749; A01H 5/02
See application file for complete search history.

*Primary Examiner* — Keith O. Robinson
(74) *Attorney, Agent, or Firm* — Cassandra Bright

(57) ABSTRACT

A new and distinct hybrid tea *Rosa* cultivar named 'ALTland' is disclosed, characterized by distinctive fully double pink flowers. Plants are vigorous, have an early flowering cycle and can be grown on their own roots. Plants flower continuously and exhibit good resistance to blackspot diseases. The new variety is a *Rosa*, normally produced as an outdoor garden or container plant.

1 Drawing Sheet

Latin name of the genus and species: *Rosa hybrida.*
Variety denomination: 'ALTland'.

BACKGROUND OF THE INVENTION

The new *Rosa* cultivar is a product of a planned breeding program conducted by the inventor, Peter Ping Lim. The objective of the breeding program was to produce vigorous new garden floribunda rose varieties for ornamental commercial applications. The cross resulting in this new variety was made during May of 2013.

The seed parent is the unpatented variety *Rosa* 'Raspberry Vigorosa'. The pollen parent is the variety *Rosa* 'RADTKO', U.S. Plant Pat. No. 16,202. The new variety was selected in 2014 by the inventor in a group of seedlings resulting from the 2013 crossing, in a nursery in Vista, Calif.

At the time of this filing plants of 'ALTland' have not been publicly released. The first sale is expected March of 2019 in the United States. Information about the new variety was published in *American Rose Magazine* October of 2017. This publication, however, was not accompanied by any public access to plant material.

Asexual reproduction of the new cultivar was performed by terminal vegetative cuttings. This was first performed at a research greenhouse in in Vista, Calif. in June 2014 and has shown that the unique features of this cultivar are stable and reproduced true to type in more than 5 successive generations.

SUMMARY OF THE INVENTION

The cultivar 'ALTland' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALTland'. These characteristics in combination distinguish 'ALTland' as a new and distinct *Rosa* cultivar:

1. Double pink flowers.
2. Vigorous plants.
3. Earlier blooming.
4. Dark glossy foliage resistant to black spot and powdery mildew disease.
5. Continuous flowering.
6. Plants do not require grafting to thrive and can be grown on their own roots.

Plants of the new cultivar 'ALTland' are similar to plants of the seed parent, in most horticultural characteristics, however, plants of the new cultivar 'ALTland' differ in the following:

1. Petal quantity of the new variety is higher than petal quantity of the seed parent.
2. Petal color of the new variety is lighter pink than that of the seed parent.

Plants of the new cultivar 'ALTland' are similar to plants of the pollen parent in most horticultural characteristics, however, plants of the new cultivar 'ALTland' differs in the following;

1. Petal quantity of the new variety is 70-80, petal quantity of the pollen parent is 23 on average.
2. Petal color of the new variety is a different color, red-purple with a white basal blotch, instead of red with a yellow basal blotch.

COMMERCIAL COMPARISON

Plants of the new cultivar 'ALTland' can be compared to the commercial variety *Rosa* 'Flower Carpet', U.S. Plant Pat. No. 7,282. These varieties are similar in most horticultural characteristics, however 'ALTland' differs in the following:

1. Petal quantity of the new variety is 70-80, petal quantity of this comparator is 10-15.
3. This comparator develops into a taller plant than 'ALTland'.
4. This comparator has a later blooming flower cycle.

Plants of the new cultivar 'ALTland' can also be compared to the unpatented variety *Rosa* 'Nearly Wild'. These varieties are similar in most horticultural characteristics, however 'ALTland' differs in the following:

1. Petal quantity of the new variety is 70-80, petal quantity of this comparator is 5.
2. This comparator has a flower with a white eye, not found in 'ALTland'.

BRIEF DESCRIPTION OF THE PHOTOGRAPH

The accompanying photograph illustrates in full color a close up of an individual flower, about 2 days old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'ALTland' plants grown outdoors, in Palm Desert, Calif. The growing temperature ranged from approximately 10° C. to 38° C. during the day and from approximately 5° C. to 22° C. during the night. Measurements were taken in September. General light conditions were very bright, normal sunlight. Measurements and numerical values represent averages of typical plant types.

Botanical classification: *Rosa* 'ALTland'.

Market classification: Floribunda.

PROPAGATION

Time to initiate roots: About 15 days at approximately 20° C.

Time to produce a rooted cutting: About 35 days at approximately 20° C.

PLANT

Age of plant described: Approximately 2 years.

Growth habit: Compact spreading.

Container size: 2 gallon.

Height: 30 cm.

Plant spread: 55 cm.

Rootstock: Own root.

Growth rate: Moderate.

Branching characteristics: Sympodial branching.

Length of primary lateral branches: Average 15 cm.

Diameter of lateral branches: 3 to 5 mm.

Quantity branches: 3 to 4 main branches, 5 to 7 lateral branches per main branch.

Branches-young wood:

*Diameter.*—Approximately 3 mm.

*Texture.*—Glabrous, thorny.

*Approximately density/quantity of thorns.*—Approximately 3 per linear cm.

*Color.*—Near RHS Green 138A.

Branches-old wood:

*Diameter.*—0.5 to 1 cm.

*Color.*—Near RHS Greyed-Green 197A.

*Texture.*—Rough thick woody striations.

*Thorns.*—

*Approximately density/quantity of thorns.*—Approximately 5 per linear cm.

*Color of thorns.*—Immature: RHS Greyed-Purple 184B. Mature: Near RHS Greyed-Orange 166D.

*Shape.*—Deltoid, moderately hooked.

*Height.*—Average 5 mm.

*Diameter.*—Base near 5 mm. Tip near 0.2 cm.

FOLIAGE

Leaf:

*Arrangement.*—Alternate and compound.

*Quantity.*—Average 5 to 9 per main branch.

*Internode length.*—Average 2 cm.

*Average length.*—6.5 cm.

*Average width.*—4 cm.

Rachis:

*Average length.*—3.5 cm.

*Average diameter.*—Approximately 0.1 cm.

*Color.*—Near RHS Green 138A.

*Texture.*—Glabrous all surfaces.

Leaflet:

*Quantity.*—5 per leaf.

*Average length.*—3 cm.

*Average width.*—2 cm.

*Shape of blade.*—Ovate.

*Apex.*—Acute.

*Base.*—Rounded.

*Margin.*—Serrate.

*Appearance of top surface.*—Slightly glossy.

*Appearance of bottom surface.*—Matte.

*Texture of top surface.*—Glabrous.

*Texture of bottom surface.*—Glabrous.

*Color.*—Young foliage upper side: Near RHS Green 137A. Young foliage under side: Near RHS Green 137C. Mature foliage upper side: Near RHS Green 137A. Mature foliage under side: Near RHS Green 137C.

*Venation.*—Type: Reticulate. Venation color upper side: Near RHS Green 137C. Venation color under side: Near RHS Green 137C.

Petiole:

*Average length.*—1.5 cm.

*Average diameter.*—0.1 cm.

*Color.*—Near RHS Green 137C.

*Texture.*—Glabrous.

FLOWER

Natural flowering season: Spring until Autumn.

Inflorescence type and habit: Single occurring, 2 to 4 fully double rotate flowers.

Rate of flower opening: Approximately 4 days from bud to fully opened flower.

Flower longevity on plant: 10 to 14 days, after fully opened.

Quantity of flowers: 20 to 25 fully opened flowers and buds.

Flower size:

*Diameter.*—Approximately 5 cm.

*Height.*—Approximately 2 cm.

Peduncle:
*Length.*—3 cm.
*Diameter.*—0.2 cm.
*Color.*—Near RHS Green 138B.

Petals:
*Petal arrangement.*—Multiple rotate, overlapping whorls.
*Petal quantity.*—70 to 80.
*Length.*—2 to 3 cm.
*Width.*—1.5 to 2.5 cm.
*Shape.*—Somewhat broad ovate.
*Margin.*—Entire, slight downward curve.
*Apex.*—Rounded, sometimes notched with age.
*Base.*—Broad attenuate.
*Texture.*—Glabrous all surfaces.

Color:
*Petals.*—When opening: Upper surface: Near RHS Red-Purple 62C. Very small basal blotch near White 155D. Lower surface: Near RHS Red-Purple 68B. Small basal blotch near White 155D. Fully opened: Upper surface: Near RHS Red-Purple 62B, base White 155D. No basal blotch. Lower surface: Near RHS Red-Purple 68A, base White 155D. No basal blotch. Fading: Upper surface: Near RHS Purple 75A, base White 155D. Lower surface: Near RHS Purple 75C, base White 155D.

Bud:
*Shape.*—Ovate.
*Length.*—Approximately 1.5 cm.
*Diameter.*—Approximately 1 cm.
*Color.*—Near RHS Red-Purple N66A.

Sepals:
*Quantity.*—5.
*Length.*—1.5 cm.
*Width.*—1.0 cm.
*Shape.*—Deltoid.
*Apex.*—Apiculate.
*Margin.*—Entire, to deeply dentate near apex.
*Color.*—Interior Surface: Near Green RHS 138C. Exterior Surface: Near Green RHS 138A.
*Texture.*—Densely and minutely pubescent upper and lower surfaces.
*Sepal extensions.*—Medium.

Receptacle:
*Length.*—0.5 cm.
*Width.*—0.5 cm.
*Shape.*—Flattened dome.
*Color.*—Near RHS Green 138C.

Profile of lower part of flower: Flattened convex.

Fragrance: Weak floral scent.

REPRODUCTIVE ORGANS

Stamens:
*Quantity.*—Average range 20 to 30.
*Filament length.*—Approximately 0.4 cm.
*Filament color.*—Near RHS White 155D.

Anthers:
*Length.*—0.1 cm.
*Shape.*—Narrow globular.
*Color.*—Near RHS White 155D.
*Pollen.*—Color: Near RHS White 155D. Quantity: Scant.

Pistil:
*Length.*—Approximately 0.8 cm.
*Style.*—Length: Approximately 0.4 cm. Color: Near RHS Green 138C.
*Stigma.*—Shape: Linear. Color: Near RHS Green 138C. Ovary color: Near RHS Green 138C. Ovary shape: Oblong. Ovary length: Average 0.4 cm. Ovary diameter: Average 0.2 cm.

OTHER CHARACTERISTICS

Seeds and fruits: Not observed.

Disease/pest resistance: Good overall disease resistance to normal pests and diseases typical of garden roses has been observed in trial settings. Very good resistance to black-spot diseases. While plants have been observed in trial settings, tests to determine exact pathogen resistance have not been conducted. Assumed pathogens the new variety exhibits resistance to included *Spaerotheca pannosa* and *Diplocarpon rosae,*

What is claimed is:

1. A new and distinct floribunda Rose cultivar plant named 'ALTland' as herein illustrated and described.

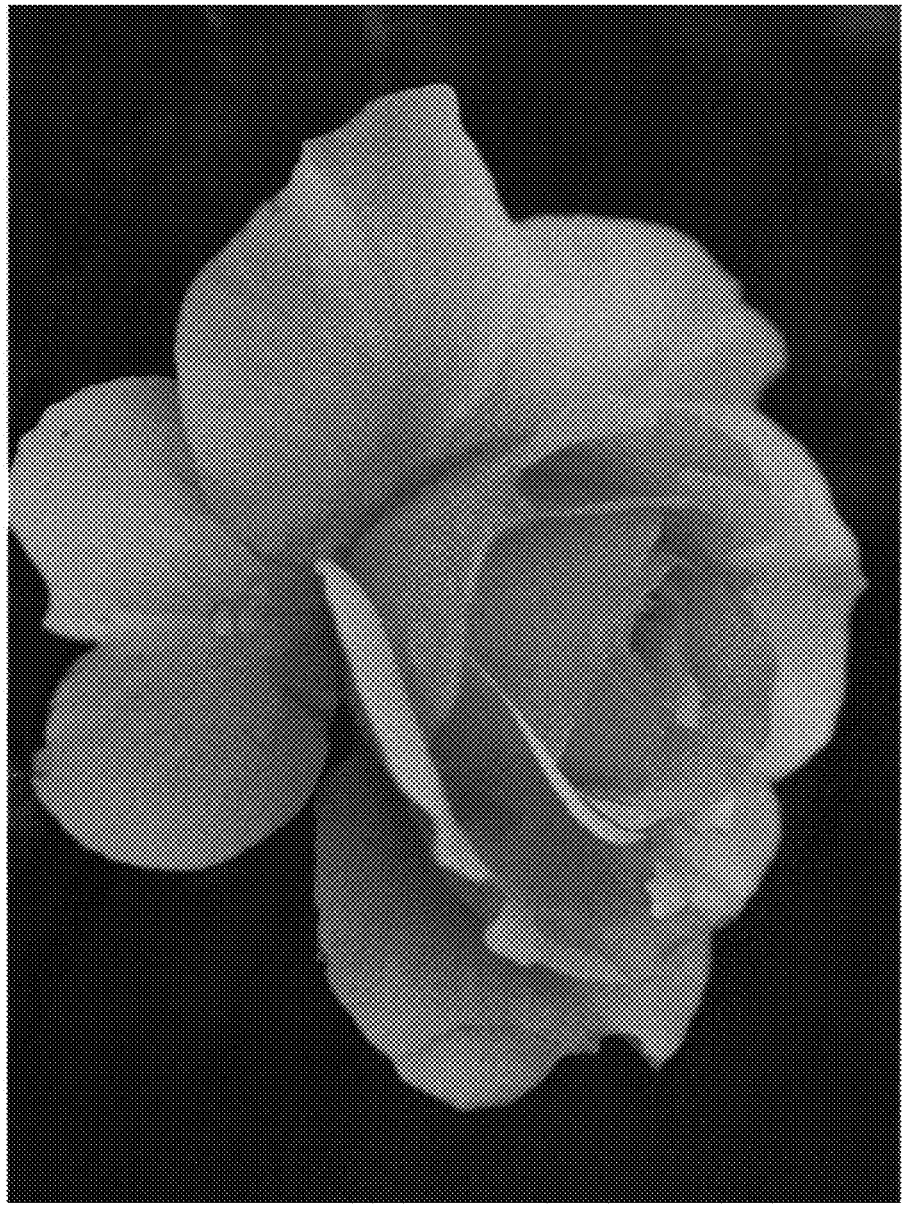

* * * * *